United States Patent [19]

Kaplan

[11] Patent Number: 4,564,636

[45] Date of Patent: Jan. 14, 1986

[54] DIPHENYLAZOMETHINES AND PHARMACEUTICAL COMPOSITIONS CONTAINING THEM

[75] Inventor: Jean P. Kaplan, Bourg la Reine, France

[73] Assignee: Synthelabo, Paris Cedex, France

[21] Appl. No.: 599,799

[22] Filed: Apr. 13, 1984

[30] Foreign Application Priority Data

Apr. 14, 1983 [FR] France ................ 83 06081

[51] Int. Cl.$^4$ ............. C07C 101/30; C07C 103/29; C07C 119/14; A61K 31/195; A61K 31/165; A61K 31/135

[52] U.S. Cl. ................ 514/567; 564/165; 564/269; 562/440; 514/620; 514/641

[58] Field of Search ............ 564/269, 165; 562/440; 514/567, 620, 641

[56] References Cited

U.S. PATENT DOCUMENTS

| | | | |
|---|---|---|---|
| 4,094,992 | 6/1978 | Kaplan et al. | 564/165 |
| 4,130,586 | 12/1978 | Isshiki et al. | 564/269 |
| 4,361,583 | 11/1982 | Kaplan | 424/319 |
| 4,400,394 | 8/1983 | Kaplan et al. | 424/319 |
| 4,400,536 | 8/1983 | Kaplan et al. | 564/269 |

FOREIGN PATENT DOCUMENTS 1529564  4/1975  United Kingdom .

OTHER PUBLICATIONS

Renzi, G. et al., *Boll. Chim. Farm.* (1976) 115(3) pp. 383–389.

*Primary Examiner*—Natalie Trousof
*Assistant Examiner*—L. Hendriksen
*Attorney, Agent, or Firm*—Wegner & Bretschneider

[57] ABSTRACT

Diphenylazomethines of the formula (I)

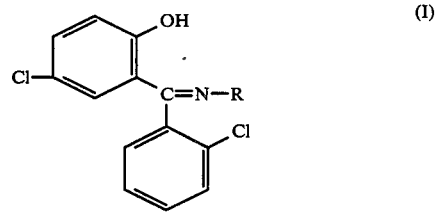

in which R represents $-(CH_2)_4OH$, $-(CH_2)_2-CHOH-CH_3$, $-CH_2-CHOH-C_2H_5$, $-CH_2-CHOH-CH_2-COOH$, $-CH_2-CHOH-CH_2-CONH_2$, $-CH_2-CH_2-CHOH-CH_2OH$ or $-CH_2-CHOH-COOH$ (in the form of the racemate or of an optically active isomer when the compound contains an asymmetric carbon) act on the central nervous system and find use as antidepressants and anticonvulsants.

2 Claims, No Drawings

DIPHENYLAZOMETHINES AND PHARMACEUTICAL COMPOSITIONS CONTAINING THEM

The present invention relates to substituted diphenylazomethines, their preparation and their therapeutic use.

The diphenylazomethines according to the invention correspond to the formula (I):

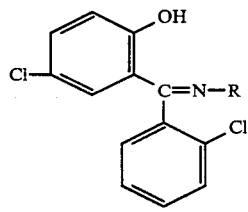

(I)

in which R represents —(CH$_2$)$_4$OH, —(CH$_2$)$_2$—CHOH—CH$_3$, —CH$_2$—CHOH—C$_2$H$_5$, —CH$_2$—CHOH—CH$_2$—COOH, —CH$_2$—CHOH—CH$_2$CONH$_2$, —CH$_2$—CH$_2$—CHOH—CH$_2$OH or CH$_2$—CHOH—COOH.

Those compounds of formula (I) which contain an asymmetric carbon may exist in the racemic form or in the form of their enantiomers.

According to the invention, the diphenylazomethines of formula (I) are prepared by a process which comprises reacting a benzophenone of the formula

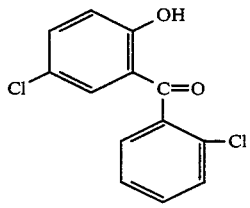

with a compound of the formula H$_2$N—R, if appropriate in the optically active enantiomer form. The reaction can be carried out at a temperature from 30° to 120° C. in a solvent such as ether, methanol, ethanol or toluene.

The Examples which follow illustrate the invention. The structures of the compounds were confirmed by analyses and IR and NMR spectra. The starting benzophenone is described in French Pat. No. 75/24,065. The compounds RNH$_2$ are described in the literature.

EXAMPLE 1

4-{[(2-Chlorophenyl)-(5-chloro-2-hydroxyphenyl)-methylene]amino}-butan-1-ol 8 g (0.03 mol) of (2-chlorophenyl)-5-chloro-2-hydroxy-phenyl)-methanone, 150 ml of ether and 4 g (0.048 mol) of 4-aminobutan-1-ol are introduced into a 500 ml flask.

The reaction mixture is brought to the boiling point and the solvent is evaporated. The residue is purified by chromatography on a silica column, the column being eluted with a mixture of chloroform/ethyl acetate. The fractions containing the intended product are combined and evaporated to dryness. An oil is obtained, which is crystallised in petroleum ether.

Melting point (Mettler)=91.8° C.

EXAMPLE 2

4-{[(2-Chlorophenyl)-(5-chloro-2-hydroxyphenyl)-methylene]amino}-butan-2-ol

A mixture of 3.4 g of (2-chlorophenyl)-(5-chloro-2-hydroxyphenyl)-methanone, 1.07 g of 4-aminobutan-2-ol and 200 ml of methanol is brought to the reflux temperature.

The progress of the reaction is followed by chromatography (TLC) and 4-aminobutan-2-ol is added regularly until the ketone disappears from the TLC.

The mixture is evaporated to dryness, the residue is partitioned between water and methylene chloride, the organic phase is decanted, dried over MgSO$_4$ and filtered and the filtrate is evaporated to dryness. The product is purified on a silica column with ethyl acetate as the eluant and the product is recrystallised from pentane, after treatment with vegetable charcoal.

Melting point=71.5°–73.5° C.

The enantiomers of this compound were prepared in the same manner by a reaction between (2-chlorophenyl)-(5-chloro-2-hydroxyphenyl)-methanone and the enantiomers of 4-aminobutan-2-ol.

The structure and properties of compounds according to the invention are shown in the following Table.

TABLE

| Compound | R | Melting point (°C.) |
|---|---|---|
| 1 | (CH$_2$)$_4$OH | 91.8° C. (Mettler) |
| 2 | (CH$_2$)$_2$—CHOH—CH$_3$ | 71.5–73.5° C. (Tottoli) |
| 3 (S) | (CH$_2$)$_2$—CHOH—CH$_3$ | 52.5–53° C. (Tottoli) $\alpha_D^{20} = +15.3°$ (c = 1, CHCl$_3$) |
| 4 (R) | (CH$_2$)$_2$—CHOH—CH$_3$ | 53–53.5° C. (Tottoli) $\alpha_D^{20} = -14.8°$ (c = 1.082; CHCl$_3$) |
| 5 | CH$_2$—CHOH—C$_2$H$_5$ | 64–66° C. (Tottoli) |
| 6 | CH$_2$—CHOH—CH$_2$—COOH | 145–146° C. (Tottoli) |
| 7 | CH$_2$—CHOH—CH$_2$—CONH$_2$ | 108–109° C. (Tottoli) |
| 8 | CH$_2$CH$_2$—CHOH—CH$_2$OH | viscous oil |
| 9 | CH$_2$—CHOH—COOH | 234° C. (decomposition) in the form of the sodium salt |

Diphenylazomethines according to the invention have been subjected to pharmacological tests demonstrating their action on the central nervous system.

The acute toxicity was determined on mice by intraperitoneal administration. The LD$_{50}$ (50% lethal dose) varies from 200 to 600 mg/kg.

The antidepressive activity of the compounds was demonstrated by antagonism to head twitches caused by L-5-hydroxytrlyptophan (L-5-HTP) in mice.

The mice (CDI males, Charles River France; 18–22 g body weight) received increasing doses of the products to be studied, or the solvent, subcutaneously, together with L-5-HTP in a dose of 250 mg/kg. 45 minutes after this injection of L-5-HTP, the number of head twitches of each mouse is counted for one minute.

For each treatment, the average number of head twitches and the percentage variation relative to a control group are calculated.

The $AD_{50}$ (50% active dose or dose which reduces the average number of head twitches by 50%) is determined from the dose-effect curve by the graphical method of Miller and Tainter (1944).

The $AD_{50}$ on intraperitoneal administration of the compounds according to the invention varies from 20 to 40 mg/kg.

The anticonvulsive activity of the compound was demonstrated by antagonism to the mortality induced by bicuculline in mice.

Bicuculline is a relatively selective blocker of postsynaptic GABA-ergic receptors and its convulsive and lethal effects are antagonised by compounds which increase the level of cerebral GABA or have a GABA-mimetic activity.

The 50% active dose ($AD_{50}$), that is to say the dose which protects 50% of the animals from the effect of bicuculline, of the substances studied was evaluated.

The $AD_{50}$ on intraperitoneal administration of the compounds according to the invention varies from 20 to 100 mg/kg.

The compounds according to the invention are active as antidepressants and anticonvulsants and also have anxiolytic, analgesic and antiinflammatory properties. They can be used in human and veterinary therapy for the treatment of various diseases of the central nervous system, for example for the treatment of depressions, psychoses and some neurological diseases, such as epilepsy, spasticity and diskinesia.

The invention accordingly relates to all pharmaceutical compositions containing the compounds (I) as active principles together with any excipients suitable for their administration, in particular oral (tablets, coated tablets, gelatin capsules, capsules, cachets and solutions or suspensions for oral use) or parenteral administration.

The daily posology may be from 250 to 5,000 mg.

I claim:

1. A diphenylazomethine of the formula

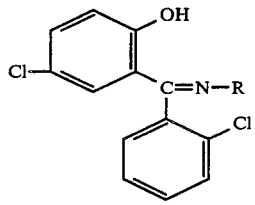

wherein R is selected from the group consisting of $-CH_2-CHOH-CH_2-COOH$, $-CH_2-CHOH-CH_2CONH_2$, $-CH_2-CH_2-CHOH-CH_2OH$, and $-CH_2CHOH-COOH$, in the form of a racemate or of an optically active isomer.

2. A pharmaceutical composition for treating depression comprising an antidepressant effective amount of a diphenylazomethine of the formula

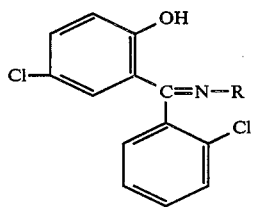

wherein R is selected from the group consisting of $-(CH_2)_4OH$, $-(CH_2)_2-CHOH-CH_3$, $-CH_2-CHOH-C_2H_5$, $-CH_2-CHOH-CH_2-COOH$, $-CH_2-CHOH-CH_2CONH_2$, $-CH_2-CH_2-CHOH-CH_2OH$, and $-CH_2-CHOH-COOH$, in the form of a racemate or of an optically active isomer when said diphenylazomethine contains an asymmetric carbon and a pharmaceutically acceptable carrier.

* * * * *